(12) United States Patent
Kim

(10) Patent No.: US 7,820,656 B2
(45) Date of Patent: Oct. 26, 2010

(54) PHARMACEUTICAL COMPOSITION COMPRISING N-ARYL N' MORPHOLINO/PIPERIDINO THIOCARBAMIDE DERIVATIVES FOR TREATING TYPE II DIABETES

(75) Inventor: Sung-Jin Kim, 10-1-2003 Hanshin Apt. 60, Chungryangri-dong, Dongdaemun-gu, Seoul (KR)

(73) Assignee: Sung-Jin Kim, Seongnam (KR)

( * ) Notice: Subject to any disclaimer, the term of this patent is extended or adjusted under 35 U.S.C. 154(b) by 621 days.

(21) Appl. No.: 11/315,696

(22) Filed: Dec. 22, 2005

(65) Prior Publication Data
US 2006/0142285 A1 Jun. 29, 2006

(30) Foreign Application Priority Data
Dec. 27, 2004 (KR) .................. 10-2004-0112874

(51) Int. Cl.
*A61K 31/535* (2006.01)
*A61K 31/17* (2006.01)
*A61K 31/175* (2006.01)

(52) U.S. Cl. .............. 514/231.2; 514/580; 514/581; 514/582; 514/585; 514/866

(58) Field of Classification Search ............ 514/231.2, 514/580, 581, 582, 585
See application file for complete search history.

(56) References Cited

U.S. PATENT DOCUMENTS
2004/0063954 A1  4/2004  Patel et al.
2005/0215573 A1  9/2005  Schilling et al.

OTHER PUBLICATIONS

Kharizanova et al., "Antitubercular activity of thiocarbamide derivatives", Famatsiya (Sofia, Bulgaria), vol. 19, No. 1, pp. 33-38 (1969).*

* cited by examiner

*Primary Examiner*—Kevin Weddington

(57) ABSTRACT

Disclosed is a medicament comprising N-aryl N' morpholino/piperidino thiocarbamide derivatives represented by the following formula 1 for preventing and treating diabetes, diabetic complications, insulin resistance and insulin resistance syndrome, and can be used in drugs, foods, and beverages inducing an effect of preventing and treating diabetes, diabetic complications, insulin resistance and insulin resistance syndrome of modern people who suffer from the increasing development of diabetes resulting from environmental factors, such as intake of westernized foods, obesity, and so on:

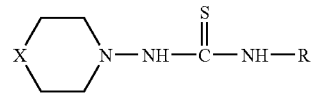

wherein, X is O or C, and R represents 4-chlorophenyl, 2-methylphenyl, 3-methoxypheny, 3-methylphenyl, or phenyl group.

11 Claims, 3 Drawing Sheets

Liver of a mouse

IP: anti-IR

Blot: anti-pTyr

← Iβ-subunit

Control   CPMT

PHARMACEUTICAL COMPOSITION COMPRISING N-ARYL N' MORPHOLINO/PIPERIDINO THIOCARBAMIDE DERIVATIVES FOR TREATING TYPE II DIABETES

CROSS-REFERENCE TO RELATED APPLICATIONS

This application claims benefit under 35 U.S.C. §119 from Korean Patent Application No. 2004-112874, filed on Dec. 27, 2004, the entire content of which is incorporated herein by reference.

BACKGROUND OF THE INVENTION

1. Field of the Invention

The present invention relates to a pharmaceutical composition comprising N-aryl N' morpholino/piperidino thiocarbamide derivatives for preventing and treating diabetes, diabetic complications, insulin resistance and insulin resistance syndrome.

2. Description of the Related Art

Diabetes mellitus is a severe chronic metabolic abnormality. There were 194 million diabetic patients and more than 300 million people exposed to a risk of developing diabetes around the world in the year 2003. WHO predicted that diabetic population would increase to 333 million by 2025 (Yakup Daily, Aug. 28, 2003). About 90% of diabetic patients have type II diabetes mellitus (World Health Organization, Fact sheet 236, http://www.who.int/inf-fs/en/fact236.html 1999; Accessed Jul. 25, 2002). It is assumed that the annual costs needed for treating diabetic patients aged between 20 and 79 amount to minimum 153 billion dollars. It is expected that this medical expenses will reach from 213 billion to 396 billion dollars at 2025. Considering that enormous medical expenses are spent and many people are exposed to diabetes, the development of drugs for preventing and treating diabetes and diabetic complications is in urgent need.

Type I diabetes mellitus is an immune-mediated disease caused by chronically and selectively destroyed pancreatic β-cells. As a consequence, a destruction of β-cells secreting insulin results in insulin deficiency that leads to hyperglycemia, diabetes, polydipsia and weight loss, and so on. Diabetic complications are loss of eyesight, renal failure, neurological disorders, heart disease, etc.

In case of type II diabetes mellitus, the first shown dysfunction is insulin resistance that insulin-sensitive cells do not respond to insulin of normal level (Consensus Development conference on Insulin Resistance 5-6 Nov. 1997, American Diabetes Association, Diabetes Care, 1998; 21:310-314). Pancreatic β-cells increase insulin secretion in order to overcome such insulin resistance. But, as time passes, β-cell function lowers, consequently insulin secretion decreases, resulting in a hyperglycemia. Type II diabetes mellitus is complexly caused by insulin-mediated suppression dysfunction of hepatic glucose excretion, insulin-mediated glucose uptake disorders into muscle and adipose cells, and β-cell dysfunction (DeFronzo R A, Bonadonna R C, Ferrannini E, Pathogenesis of NIDDM, A balanced overview, Diabetes Care, 1992; 15: 318-368). And, this insulin resistance is an important cause in the development of various metabolic diseases. Insulin resistance indicates that a tissue response to insulin actions decreases, and the resultant symptoms are called insulin resistance syndrome (IRS), syndrome X, metabolic syndrome, plurimetabolic syndrome, new world syndrome, syndrome X+, deadly quartet, or diabesity (Zimmet, P. Addressing the insulin resistance syndrome. A role for the thiazolidinediones, 2002). Insulin resistance is accompanied with insulin-mediated glucose uptake disorders, glucose intolerance, hyperinsulinemia, triglyceride (very low density lipoprotein triglyceride) increase, HDL cholesterol decrease, hypertension, and so on (Reaven, G. M. Banting lecture. Role of insulin resistance in human disease. Diabetes 37, 1595-1607, 1988). Insulin resistance syndrome contains systemic obesity, central obesity, upper abdominal obesity, arteriosclerosis, acanthosis nigricans, polycystic ovarian syndrome, hyperuricemia, PAI-1 (plasminogen activator inhibitor-1) increase, thrombolystic abnormality, endothelial and smooth muscle dysfunction, microalbuminuria, and so on (Peter, P., Nuttall, S. L., Kendall, M. J. Insulin resistance—the new goal!. J. Clinical Pharmacy and Therapeutics 28, 167-174, 2003). According to a recent study, it is suggested that insulin resistance cause the following diseases: sleep apnoea (Punjabi, N. M., Ahmed, M. M., Polotsky, V. Y., Beamer, B. A., O'Donnell, C. P. Sleep-disordered breathing, glucose intolerance, and insulin resistance. Respiratory Physiology & Neurobiology 136, 167-178, 2003); prostate cancer (Barnard, R. J., Aronson, W. J., Tymchuk, C. N., Ngo, T. H. Prostate cancer: another aspect of the insulin-resistance syndrome, Obesity reviews 3, 303-308, 2002); type I diabetes (Greenbaum, C. J. Insulin resistance in type 1 diabetes. Diabetes Metab. Res. Rev. 18, 192-200, 2003); affective disorders (Rasgon, N., Jarvik, L. Insulin resistance, affective disorders, and Alzheimer's disease: review and hypothesis. J. Gerontol. A Biol. Sci. Med. Sci. 59, 178-183, 2004); Alzheimer's disease (Watson, G. S., Craft, S. The role of insulin resistance in the pathogenesis of Alzheimer's disease: implications for treatment. CNS Drugs. 17, 27-45, 2003); stroke (Kernan, W. N., Inzucchi, S. E., Viscoli, C. M., Brass, L. M., Bravata, D. M., Horwits, R. I. Insulin resistance and risk for stroke. Neurology 59, 809-815, 2002); breast cancer (Stoll, B. A. Upper abdominal obesity, insulin resistance and breast cancer risk. Int. J. Obes. Relat. Metab. Disord. 26, 747-753, 2002); inflammation (Perseghin, G., Petersen, K., Shulman, G. I. Cellular mechanism of insulin resistance: potential links with inflammation. Int. J. Obes. Relat. Metab. Disord. 27 Suppl. 3, S6-S11, 2003); rheumatoid arthristis (Dessein, P. H., Joffe, B. I., Stanwix, A. E. Inflammation, insulin resistance, and aberrant lipid metabolism as cardiovascular factors in rheumatoid arthristis. J. Rheumatol. 30, 1403-1405, 2003); etc. Accordingly, a substance capable of preventing and treating insulin resistance can be used as medicament for preventing and treating the above insulin resistance syndrome.

According to a recent study, it is disclosed in many reports that some chemical substances containing morpholine have an effect of improving diabetes and insulin resistance. For example, it is suggested that PPMP (DL-threo-1-phenyl-2-palmitoylamino-3-morpholino-1-propanol) have an effect on the treatment of TNF-induced insulin resistance (Grigsby, R. J., Dobtowsky, R. T. Inhibition of ceramide production reverses TNF-induced insulin resistance. Biochem. Biophys. Res. Commun. 287, 1121-1124, 2001) and SIN-1 (3-morpholino sydnonimine) be acted as an insulin promoter in a liver (Guarino, M. P., Afonso, R. A., Raimundo, N., Raposo, J. F., Macedo, M. P. Hepatic glutathione and nitric oxide are critical for hepatic insulin-sensitizing substance action. Am. J. Physiol. Gastrointest. Liver Physiol. 284, G588-G594, 2003). In addition, it is suggested that some chemical substances containing a piperidine structure have a blood glucose lowering action (Rynbrandt, R. H., Schmidt, F. L., Szmuszkovicz, J. cis-1-(2-(p-anisidinomethyl)cyclohexyl)piperidine and related compounds. Oral hypoglycemic agents. J. Med. Chem. 14, 985-987; Srivastava, V., Suresh, A. J., Pandeya, S.

N., Pandey, A. Evaluation of some acylamide derivatives as potential hypoglycemic agents. Boll. Chim. Farm. 135, 452-457, 1996).

SUMMARY OF THE INVENTION

An object of the present invention is to provide N-aryl N' morpholino/piperidino thiocarbamide derivatives capable of preventing and treating diabetes, diabetic complications, insulin resistance and insulin resistance syndrome, which is safe without toxicity.

BRIEF DESCRIPTION OF THE DRAWINGS

The above aspects and features of the present invention will be more apparent by describing certain embodiments of the present invention with reference to the accompanying drawings, in which.

DETAILED DESCRIPTION OF THE PREFERRED EMBODIMENTS

Figure 1:
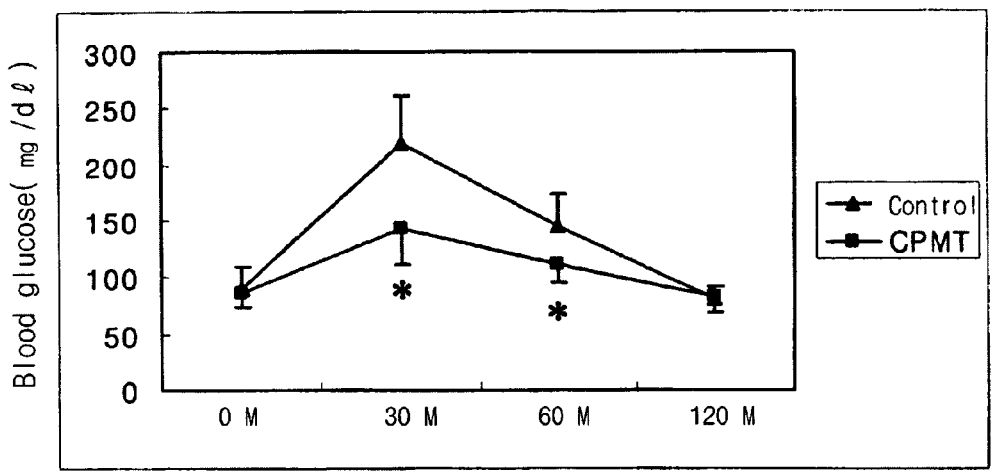
FIG. 1 illustrates a blood glucose lowering effect of N(4'-chlorophenyl) N' morpholino thiocarbamide through an oral glucose tolerance test. The value is an average±standard deviation (n=5) and significance to a control group is *:P<0.05.

The present invention relates to a medicament comprising N-aryl N' morpholino/piperidino thiocarbamide derivatives represented by the following formula 1 for preventing and treating diabetes, diabetic complications, insulin resistance and insulin resistance syndrome:

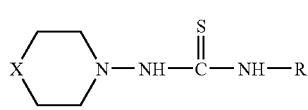

Formula 1 wherein, X is O or C, and R represents 4-chlorophenyl, 2-methylphenyl, 3-methoxypheny, 3-methylphenyl, or phenyl group.

The pharmaceutical composition of the present invention containing N-aryl N' morpholino/piperidino thiocarbamide derivatives can further comprise pharmaceutically acceptable carriers and more than one ingredient selected from a group consisting of additives according to a general method.

In addition, the present invention relates to use of N-aryl N' morpholino/piperidino thiocarbamide derivatives represented by the above formula 1, pharmaceutically acceptable salts and esters thereof as a medicament for preventing and treating diabetes, diabetic complications, insulin resistance and insulin resistance syndrome.

The compound of the present invention represented by the above formula 1 is generally prepared by adding an equal mole of aryl isothiocyanate and 1-amino morpholine or N-amino piperidine to ethanol 25 ml to be refluxed, followed by distillating an excess of ethanol to be removed, cooling the residues, and filtering solid materials to be recrystallized with ethanol.

Carriers that can be included in a pharmaceutical composition containing N-aryl N' morpholino/piperidino thiocarbamide derivatives of the present invention generally comprise materials referred to as excipients or diluents. Carriers are more than one ingredient selected from a group consisting of lactose, dextrose, sucrose, sorbitol, mannitol, xylitol, erythritol, maltitol, starch, isomerized sugar, white sugar, acacia gum, alginate, gelatin, calcium, phosphate, calcium silicate, cellulose, methyl cellulose, microcrystalline cellulose, polyvinyl pyrrolidone, water, methylhydroxybenzoate, propylhydroxybenzoate, para-oxybenzoate, methyl para-oxybenzoate, para-oxypropylbenzoate, talc, magnesium stearate and mineral oils.

Furthermore, additives that can be included in a pharmaceutical composition containing N-aryl N' morpholino/piperidino thiocarbamide derivatives of the present invention are more than one ingredient selected from a group consisting of natural carbohydrates, savoring agents, nutrients, vitamin, mineral (electrolyte), flavoring agents (synthetic and natural flavoring agent), colorant, filler (cheese, chocolate, etc), pectic acid and its salts, alginic acid and its salts, organic acid, protective colloidal thickener, pH modifier, stabilizer, antiseptic, antioxidant, glycerin, alcohol, carbonating agent, and pulp.

The pharmaceutical composition containing N-aryl N' morpholino/piperidino thiocarbamide derivatives according to the present invention can be formulated in a form of oral formulations such as powder, tablet, capsule, suspension, emulsion, syrup, aerosol, etc; external application; suppository or sterile injection according to a general method, respectively.

A daily dose of N-aryl N' morpholino/piperidino thiocarbamide derivatives can vary with patient's age, sex, and weight, and may be administered in a dose of 0.1 to 500 mg/kg once or several times a day. In addition, a dosage of N-aryl N' morpholino/piperidino thiocarbamide derivatives can be increased and decreased depending on administration routes, disease severity, sex, weight, age and so on. The above dosage is not intended to limit the scope of the invention in any way. The N-aryl N' morpholino/piperidino thiocarbamide derivatives of the present invention scarcely have toxicity and side effects, therefore can be safely used even in taking them for a long time for the purpose of prevention.

The above N-aryl N' morpholino/piperidino thiocarbamide derivatives of the present invention also can be used in various foods, beverages, gum, tea, vitamin complex supplements, and foods and beverages like health care foods together with a sitologically acceptable additives.

In foods containing N-aryl N' morpholino/piperidino thiocarbamide derivatives according to the present invention, N-aryl N' morpholino/piperidino thiocarbamide derivatives can be used in an amount of 0.1 to 15 wt %, preferably 1 to 10 wt % relative to total food weight.

In beverages containing N-aryl N' morpholino/piperidino thiocarbamide derivatives according to the present invention, N-aryl N' morpholino/piperidino thiocarbamide derivatives may be added in a ratio of 1-30 g, preferably 3-10 g based on beverage 100 ml.

Moreover, sitologically acceptable additives that can be included in the foods and beverages according to the present invention are more than one ingredient selected from a group consisting of natural carbohydrates, savoring agents, nutrients, vitamin, mineral (electrolyte), flavoring agents (synthetic and natural flavoring agent), colorant, filler (cheese, chocolate, etc), pectic acid and its salts, alginic acid and its salts, organic acid, protective colloidal thickener, pH modifier, stabilizer, antiseptic, antioxidant, glycerin, alcohol, carbonating agent, and pulp.

Said additives are preferably added in a range of 0.01-25 parts by weight per 100 parts by weight of food or beverage composition.

In addition, natural carbohydrates such as monosaccharides (glucose and fructose), disaccharides (maltose and sucrose), and polysaccharides (dextrin and cyclodextrin); and sugar alcohols such as xylitol, sorbitol, erythritol, etc can be used and are generally added in an amount of about 1-20 g, preferably about 5-12 g per beverage composition 100 ml.

Natural savoring agents such as thaumatin, stevia extracts (for example, revaudioside A, glycyrrhizin, etc); and synthetic savoring agents such as saccharins and aspartame, etc can be used as a savoring agent.

The beverage composition of the present invention puts no special limitation on liquid ingredients except that it contains the above compound and its derivatives as an essential ingredient in the indicated ratio.

The following preparative examples illustrate the invention in more detail, but the present invention is not to be limited to these examples.

Experimental Example 1

Synthesis of N(Aryl) N' Morpholino/Piperidino Thiocarbamide

1) Method

An equal mole of aryl isothiocyanate and 1-amino morpholine/N-amino piperidine are added to EtOH 25 ml and refluxed for 3 hours, followed by distillating an excess of EtOH to be removed, cooling the residues, and filtering solid materials to be re-crystallized with EtOH.

2) Result
  1) Structure

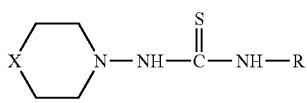

(basic structure)

TABLE 1

| R | X | Molecular formula | mp (° C.) |
|---|---|---|---|
| 4-chlorophenyl | ⟨phenyl-Cl⟩ | O | $C_{11}H_{14}N_3OSCl$ | 180 |
| 2-methylphenyl | ⟨phenyl-H₃C⟩ | O | $C_{12}H_{17}OSN_3$ | 140 |
| 3-methoxyphenyl | ⟨phenyl-OCH₃⟩ | O | $C_{12}H_{17}O_2SN_3$ | 116 |
| 3-methylphenyl | ⟨phenyl-CH₃⟩ | O | $C_{12}H_{17}OSN_3$ | 132 |
| Phenyl | ⟨phenyl⟩ | O | $C_{11}H_{15}N_3OS$ | 145 |
| Phenyl | ⟨phenyl⟩ | C | $C_{11}H_{17}N_3S$ | 145 |

Experimental Example 2

Synthesis of N(4'-chlorophenyl) N' Morpholino Thiocarbamide

1) Method

An equal mole of 4-chlorophenyl isothiocianate and 1-amino morpholine are added to EtOH 25 ml and refluxed for 3 hours, followed by distillating an excess of EtOH to be removed, cooling the residues, and filtering solid materials to be re-crystallized with EtOH.

2) Result
  1) Structure

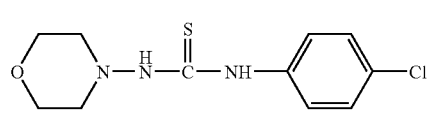

2) $^1$H-NMR data 7.598-7.61 (s) 2H, 7.40-7.41 (s) 2H, 3.64-3.70 (s) 4H, 3.4 (s) 1H, 2.51-2.74 (s) 4H, 2.4 (s) 1H 3) mp=180° C.

4) Molecular formula $C_{11}H_{14}N_3OSCl$

Experimental Example 3

Oral Glucose Tolerance Test

1) Method

A mouse was starved for 18 hours, prior to orally administering N(4'-chlorophenyl) N' morpholino thiocarbamide to the mouse in a dose of 80 mg/kg. After an hour passed, Glucose of 2 g/kg was orally administered to measure blood glucose level in 30, 60, and 120 minutes using a blood glucose testing kit.

2) Result

N(4'-chlorophenyl) N' morpholino thiocarbamide induced a remarkable blood glucose lowering effect in an oral glucose tolerance test using a mouse, as compared with that of a control group (FIG. 1).

Experimental Example 4

Blood Glucose Lowering Effect Using a Streptozotocin-Induced Diabetic Mouse

1) Method

A mouse was used two weeks after streptozotocin (50 mM citrate buffer, pH 4.5) was intraperitoneally administered to the mouse (J Gene Med. 2003, 5, 417-424). N(4'-chlorophenyl) N' morpholino thiocarbamide was orally administered in a dose of 80 mg/kg once a day for 5 days a week and given for 4 consecutive weeks. Change of blood glucose level was measured once a week.

2) Result

Figure 2:
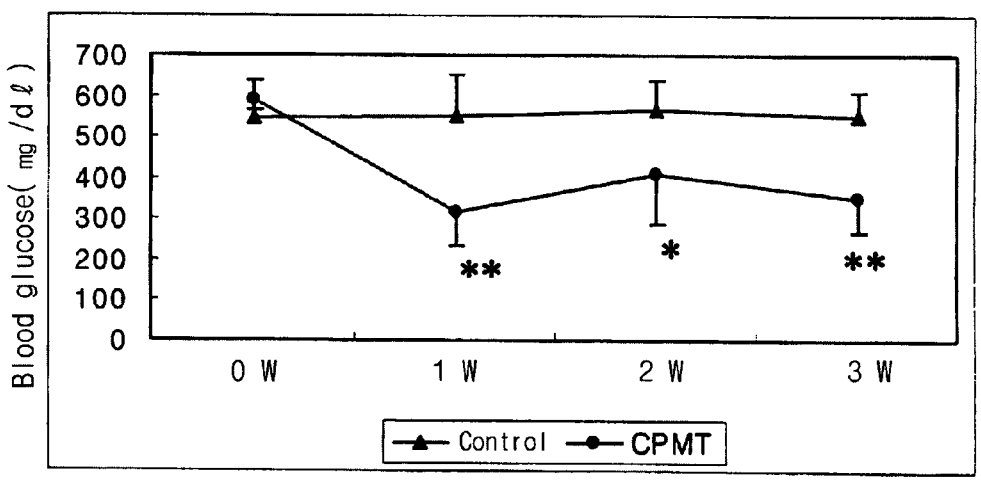
FIG. 2 illustrates a blood glucose lowering effect of N(4'-chlorophenyl) N' morpholino thiocarbamide on a STZ-induced diabetic mouse. The value is an average±standard deviation (n=5) and significance to a control group is *:P<0.05 and **:P<0.01.

Blood glucose level was measured two weeks after streptozotocin (50 mM citrate buffer, pH 4.5) was intraperitoneally administered to a mouse. The blood glucose level stayed at almost 550 mg/dl for 3 weeks. N(4'-chlorophenyl) N' morpholino thiocarbamide was orally administered in a dose of 80 mg/kg a day 5 days a week and given for 3 consecutive weeks. As a result, an administered group with N(4'-chlorophenyl) N' morpholino thiocarbamide showed blood glucose level of 300-400 mg/dl, which proved that it had a remarkable blood glucose lowering effect compared with a control group (FIG. 2).

Experimental Example 5

Measurement of Glycogenesis Ability

1) Method

Hepatocyte was dissolved in 0.1% sodium lauryl sulfates 24 hours after N(4'-chlorophenyl) N' morpholino thiocarbamide in a dose of 10 μg/ml was administered to HepG2 hepatocyte. Thereto, ethanol was added to precipitate glycogen, followed by dissolving the precipitated glycogen in conc. sulfuric acid. Glucose produced was reacted with phenol to obtain a stained product. An absorbance of the stained product was measured at 490 nm (J Applied Physiol, 1970, 28, 234-236).

2) Result

Figure 3:
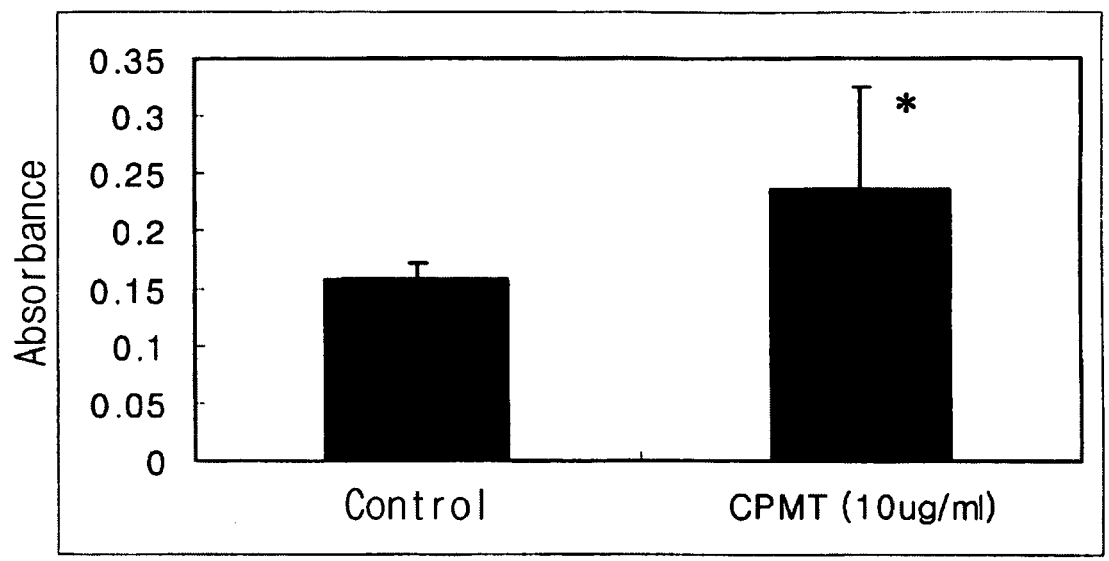
FIG. 3 illustrates a glycogenesis improvement effect of N(4'-chlorophenyl) N' morpholino thiocarbamide. The value is an average±standard deviation (n=5) and significance to a control group is *: P<0.05.

HepG2 cells (hepatocyte) were cultured to administer N(4'-chlorophenyl) N' morpholino thiocarbamide in a dose of 10 μg/ml for 24 hours, followed by measuring an absorbance at 490 nm to be evaluated according to a method by Lo et al. As a result of measuring a glycogen content, an administered group increased glycogenesis by 49.89% compared with a control group (FIG. 3). When N(4'-chlorophenyl) N' morpholino thiocarbamide was administered to HepG2 cells, the rate of ghlycogenesis increased by 56%-216% compared with that of a control group (Table 2). Accordingly, the N-aryl N' morpholino/piperidino thiocarbamide derivatives were proved to have a noticeable blood glucose lowering effect owing to the increase of glycogenesis in hepatocyte.

TABLE 2

| Glycogen Analytic Data | | | | | | |
|---|---|---|---|---|---|---|
| Administered groups | R | | X | Molecular formular | Dosage (μg/ml) | Glycogenesis (absorbance) | Rate of Increase(%) |
| Control | | | | | 0 | 0.103 | |
| 2-methylphenyl | H$_3$C- (2-methylphenyl structure) | | O | C$_{12}$H$_{17}$OSN$_3$ | 10 100 | 0216 0.238 | 110 131 |
| 3-methoxyphenyl | -OCH$_3$ (3-methoxyphenyl structure) | | O | C$_{12}$H$_{17}$O$_2$SN$_3$ | 10 100 | 0.191 0.202 | 85 96 |
| 3-methylphenyl | -CH$_3$ (3-methylphenyl structure) | | O | C$_{12}$H$_{17}$OSN$_3$ | 10 100 | 0.189 0.325 | 83 216 |

TABLE 2-continued

| | | | | | | |
|---|---|---|---|---|---|---|
| phenyl | (phenyl ring) | O | $C_{11}H_{15}N_3OS$ | 10 | 0.301 | 195 |
| | | | | 100 | 0.225 | 118 |
| phenyl | (phenyl ring) | C | $C_{12}H_{17}N_3S$ | 10 | 0.196 | 90 |
| | | | | 100 | 0.161 | 56 |

Experimental Example 6

Measurement of Lipid Peroxide (TBARS)

1) Method

HepG2 cells were cultured to administer N(4'-chlorophenyl) N' morpholino thiocarbamide (10 μg/ml-100 μg/ml). After 24 hours, a cellular culture solution was removed to wash HepG2 cells with a phosphate buffer solution (PBS), prior to adding 0.1% Triton X-100 to detach the cells. The separated cell extracts were mixed with 20% acetic acid, pH 3.5 and 0.78% aqueous thiobarbituric acid solution. The mixture was heated at 95° C. for 1 hour and centrifuged at 3000 rpm for 15 minutes. The absorbance of the red supernatant was measured at 532 nm (Anal Biochem, 1979, 95, 351-358).

2) Result

Figure 4:
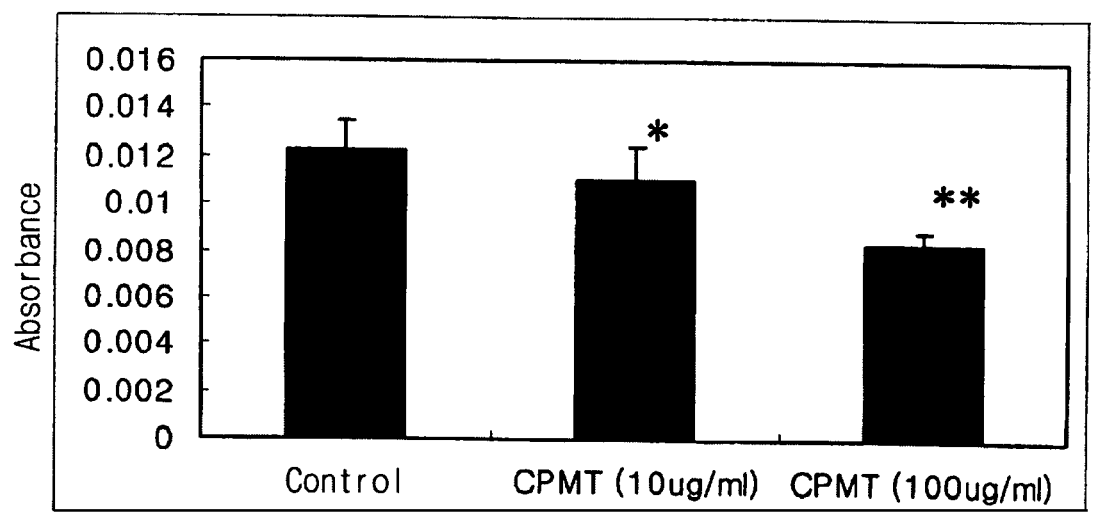
FIG. 4 illustrates an inhibitory activity effect against lipid peroxidation of N(4'-chlorophenyl) N' morpholino thiocarbamide. The value is an average±standard deviation (n=5) and significance to a control group is *:P<0.05 and **:P<0.01.
Figure 5:
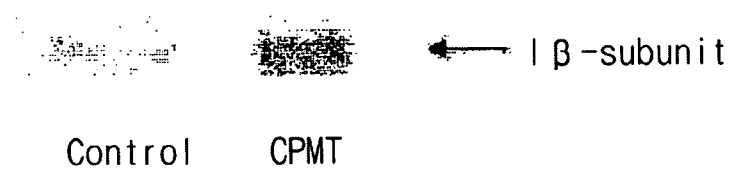
FIG. 5 illustrates an insulin receptor activity improvement effect of N(4'-chlorophenyl) N' morpholino thiocarbamide.
Figure 6:
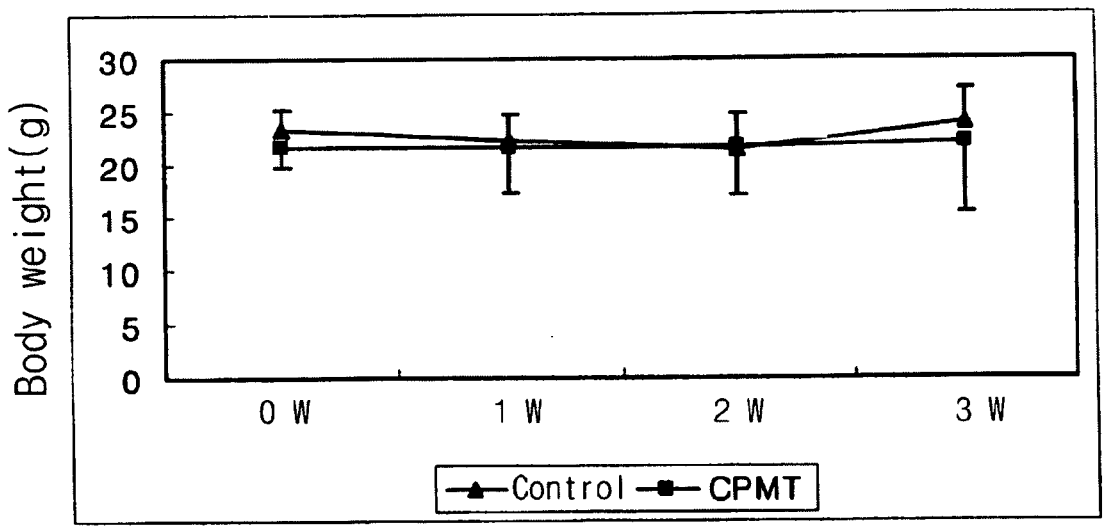
FIG. 6 illustrates an effect of N(4'-chlorophenyl) N' morpholino thiocarbamide on body weight. The value is an average±standard deviation (n=5).

When N(4'-chlorophenyl) N' morpholino thiocarbamide in a dose of 10 μg/ml and 100 μg/ml was administered to HepG2 cells, a TBARS content decreased by 10.2% and 32% respectively, as compared with that of a control group (FIG. 4). When other N-aryl N' morpholino/piperidino thiocarbamide derivatives were administered to HepG2, a TBARS content decreased by 19%-50% compared with that of a control group (Table 3). Accordingly, N-aryl N' morpholino/piperidino thiocarbamide derivatives of the present invention were proved to have a remarkable anti-oxidative effect.

TABLE 3

TBARS Analytic Data

| Administered group | R | | X | Molecular formular | Dosage (μg/ml) | Average content of TBARS (%) |
|---|---|---|---|---|---|---|
| Control | | | | | 0 | 100.0 |
| | 2-methylphenyl | H₃C-phenyl | O | $C_{12}H_{17}OSN_3$ | 10 | 57.9 |
| | | | | | 100 | 60.5 |
| | 3-methoxyphenyl | OCH₃-phenyl | O | $C_{12}H_{17}O_2SN_3$ | 10 | 81.9 |
| | | | | | 100 | 63.9 |
| | 3-methylphenyl | CH₃-phenyl | O | $C_{12}H_{17}OSN_3$ | 10 | 67.5 |
| | | | | | 100 | 66.3 |
| | Phenyl | phenyl | O | $C_{11}H_{15}N_3OS$ | 10 | 50.0 |
| | | | | | 100 | 50.0 |
| | Phenyl | phenyl | O | $C_{12}H_{17}N_3S$ | 10 | 61.4 |
| | | | | | 100 | 65.1 |

Experimental Example 7

Phosphorylation Measurement of Insulin Receptor Tyrosin Residues

1) Method

1. Preparation of Hepatic Lysate

N(4'-chlorophenyl) N' morpholino thiocarbamide in a dose of 80 mg/kg was administered to a male IC mouse starved for 16 hours. After an hour passed, the mouse was dissected to separate a liver at 4° C. Hepatic homogenization was provided by a little modification of conventional method (Zhao, H., Xu, H., Moore, E., Meiri, N., Quon, M. J., Alkon, D., L., Insulin receptors and spatial memory. J. Biol. Chem. 274, 34893-34902, 1999). The separated liver was suspended in a buffer A containing 50 mM Tris HCl, pH 7.4, 1 mM EDTA, 1 mM EGTA, 150 mM NaCl, 1% Triton X-100, 0.5 mM PMSF, 1 mM $Na_3VO_4$, leupeptin and aprotinin 1 µg/ml, and homogenized using a Potter-Elvehjem homogenizer. The lysate was centrifuged at 10,000×g for 20 minutes. The supernatant was analyzed on proteins and preserved at −70° C.

2. Immunoprecipitation

An immunoprecipitation was carried out by a known technique (Kim S. J., Kahn, C. R. Insulin stimulates phosphorylation of c-Jun, c-Fos and Fos-related proteins in cultured adipocytes. J. Biol. Chem. 269, 11887-11892, 1994). An equal amount of proteins from hepatic lysate were cultured with an insulin receptor antibody at 4° C. for 1 hour, followed by thereto adding protein A-cephalos to precipitate the immune complex by a centrifuge. The pellets were continuously washed with buffer A (0.01M Tris, pH 7.4, 1M NaCl, 1% Nonidet P-40), buffer B (0.01M Tris, pH 7.4, 0.1M NaCl, 0.01M EDTA, 1% Nonidet P-40, 0.3% SDS) and buffer C (0.01M Tris, pH 7.4 and 1% Nonidet P-40) 1 ml. The final pellets were soluble in a Laemmli buffer containing dithiothreitol 100 mM, boiled for 5 minutes, and centrifuged with a microcentrifuge, followed by performing SDS-PAGE with the supernatant and analyzing western blots using anti-pTyr antibody.

3. Western Blot Analysis

An equal amount of hepatic proteins were applied to SDS polyacrylamide gel. An electric transfer of proteins from gels to nitrocellulose sheets (Scheleicher and Schuell) was carried out at 100V (constant voltage) for an hour as described by Towbin et al (Towbin H., Staehelin, J., Gordon, J. Electric transfer of proteins from polyacrylamide gels to nitrocellulose sheets: procedure and some applications. Proc. Natl. Acad. Sci. USA 76, 4350-4354, 1979). The filter papers were probed with PBS containing 0.1% Tween 20 and 3% bovine serum albumin at 23° C. for an hour. And then, the blots were cultured with HRP conjugate anti-rabbit IgG for 30 minutes and five times washed with PBS containing Tween 20 for 10 minutes, respectively. And, the detection for fixed specific antigen was performed by ECL (NEN).

2) Result

An administered group with N(4'-chlorophenyl) N' morpholino thiocarbamide induced the noticeable tyrosin phosphorylation of insulin receptors compared with a control group. This suggests that N(4'-chlorophenyl) N' morpholino thiocarbamide remarkably stimulate activities of insulin receptors.

Experimental Example 8

Measurement of Body Weight

1) Method

Change of body weight was measured every week before and after N(4'-chlorophenyl) N' morpholino thiocarbamide (80 mg/kg, PO) was administered.

2) Result

When N(4'-chlorophenyl) N' morpholino thiocarbamide was orally administered in a dose of 80 mg/kg once a day for 3 consecutive weeks, there was no difference in body weight between an administered group and a control group. This result proves that even if the compound is administered for a long time, change of body weight is not induced.

Experimental Example 9

Measurement of Lethal Dose 50%

1) Method

The number of dead animal was counted after N(4'-chlorophenyl) N' morpholino thiocarbamide was orally administered to 10 mice per a dose in a dose of 50 mg/kg, 500 mg/kg, and 5000 mg/kg.

2) Result

Even if N(4'-chlorophenyl) N' morpholino thiocarbamide was administered in a dose of 50 mg/kg, 500 mg/kg, and 5000 mg/kg, no mouse was dead. Consequently, LD 50 is considered to be more than 5 g/kg.

Experimental Example 10

Measurement of Anti-Inflammatory Action

1) Method

Nitrites accumulated in a cellular medium were measured as a marker of nitrous oxide (NO) formation through a Griess reaction. RAW 264.7 cells were cultured in a medium containing DMEM, 10% FBS, penicillin (100 units/ml) and streptomycin sulfate (100 µg/ml) in a presence of 5% $CO_2$, treated with N-aryl N' morpholino/piperidino thiocarbamide derivatives in a content of 10 µg/ml and 100 µg/ml in a presence of LPS (1 µg/ml), followed by adding a Griess reagent 100 µl to the medium 100 µl 15 hours later to be cultured at room temperature for 10 minutes and measuring an absorbance at 540 nm. Nitrite content in a medium was evaluated by a standard curve using $NaNO_2$.

2) Result

Table 4 indicates that a content of nitrites produced by LPS was inhibited from 18.91% to 100% by the administration of the derivatives. This result suggests that these N-aryl N' morpholino/piperidino thiocarbamide derivatives have so remarkable anti-inflammatory action that they can be used in effectively preventing and treating various inflammatory reaction resulting from diabetic complication and insulin resistance.

TABLE 4

Anti-inflammation Activity

| R | X | Molecular formular | Dosage (ug/ml) | Produced nitrites(μM) | % |
|---|---|---|---|---|---|
| Control | | | | 3.3435 | 0 |
| LPS(1 μg/ml) | | | | 6.2775 | 100 |
| 4-chlorophenyl (4-Cl-C₆H₄–) | O | $C_{11}H_{14}N_3OSCl$ | 10 | 3.4845 | 4.81 |
| | | | 100 | 3.0545 | −9.85 |
| 2-methylphenyl (2-CH₃-C₆H₄–) | O | $C_{12}H_{17}OSN_3$ | 10 | 5.3155 | 81.17 |
| | | | 100 | 5.284 | 66.14 |
| 3-methoxyphenyl (3-OCH₃-C₆H₄–) | O | $C_{12}H_{17}O_2SN_3$ | 10 | 5.7255 | 81.19 |
| | | | 100 | 5.0155 | 56.99 |
| 3-methylphenyl (3-CH₃-C₆H₄–) | O | $C_{12}H_{17}OSN_3$ | 10 | 5.7255 | 81.19 |
| | | | 100 | 5.1575 | 61.83 |
| phenyl (C₆H₅–) | O | $C_{11}H_{15}N_3OS$ | 10 | 5.1735 | 62.37 |
| | | | 100 | 4.779 | 48.93 |
| phenyl (C₆H₅–) | O | $C_{12}H_{17}N_3S$ | 10 | 5.5515 | 75.26 |
| | | | 100 | 5.5205 | 74.20 |

Preparative Example 1

Tablet

According to the following composition, tablets were prepared by a general preparation.

1-1. Tablet Composition

| | |
|---|---|
| N(4'-chlorophenyl) N' morpholino thiocarbamide | 500.0 mg |
| Lactose | 500.0 mg |
| Talc | 5.0 mg |
| Magnesium stearate | 1.0 mg |

Preparative Example 2

Capsule

According to the following composition, capsules were prepared by the following method. N(4'-chlorophenyl) N' morpholino thiocarbamide was mixed with excipients, prior to filling gelatin capsules with the mixture to prepare capsules.

2-1. Capsule Composition

| | |
|---|---|
| N(4'-chlorophenyl) N' morpholino thiocarbamide | 500.0 mg |
| Starch 1500 | 10.0 mg |
| Magnesium stearate BP | 100.0 mg |

Preparative Example 3

Syrup

According to the following composition, syrup was prepared by the following method. First, white sugar was dissolved in purified water, prior to adding thereto para-oxybenzoate, para-oxypropylbenzoate and N(4'-chlorophenyl) N' morpholino thiocarbamide to be dissolved at 60° C. and cooled. Thereto, purified water was added to make up to 150 ml.

3-1. Syrup Composition

| | |
|---|---|
| N(4'-chlorophenyl) N' morpholino thiocarbamide derivative | 5.0 g |
| White sugar | 95.1 g |
| Para-oxybenzoate | 80.0 mg |
| Para-oxypropylbenzoate | 16.0 mg |
| Purified water | to 150 ml |

Preparative Example 4

Solution

The following ingredients were formulated by a general solution preparation, followed by filling brown bottles to prepare solution.

4-1. Solution Composition

| | |
|---|---|
| N(4'-chlorophenyl) N' morpholino thiocarbamide | 500.0 mg |
| Isomerized sugar | 20.0 g |
| Antioxidant | 5.0 mg |
| Methyl para-oxybenzoate | 2.0 mg |
| Purified water | to 100.0 ml |

Preparative Example 5

Powder

The following ingredients were mixed by a general powder preparation, prior to preparing powder by putting the mixture into a bag to be sealed.

5-1. Powder Composition

| | |
|---|---|
| N(4'-chlorophenyl) N' morpholino thiocarbamide | 50.0 mg |
| Lactose | 100.0 mg |
| Talc | 5.0 mg |

Preparative Example 6

Injection

Injection was prepared by filling an ample of 2.0 ml with the following ingredients to be sterilized according to a general preparation.

6-1. Injection Composition

| | |
|---|---|
| N(4'-chlorophenyl) N' morpholino thiocarbamide | 50.0 mg |
| Antioxidant | 1.0 mg |
| Tween 80 | 1.0 mg |
| Distilled water for injection | to 2.0 ml |

A pharmaceutical composition containing N-aryl N' morpholino/piperidino thiocarbamide derivatives as well as N(4'-chlorophenyl) N' morpholino thiocarbamide has an effect of preventing and treating diabetes, diabetic complications, insulin resistance and insulin resistance syndrome, and can be widely and effectively used for diabetic patients.

The foregoing embodiment and advantages are merely exemplary and are not to be construed as limiting the present invention. The present teaching can be readily applied to other types of apparatuses. Also, the description of the embodiments of the present invention is intended to be illustrative, and not to limit the scope of the claims, and many alternatives, modifications, and variations will be apparent to those skilled in the art.

What is claimed is:

1. A methods of lowering blood glucose in a patient in need thereof and/or treating Types II diabetes, said method comprising administering a pharmaceutically effective amount of a medicament to a patient in need thereof, said medicament comprising the following composition:

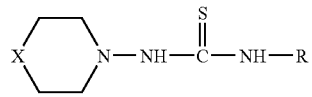

Or pharmaceutically acceptable salts or esters of said composition;

Wherein, X is O or C, and R represents 4-chlorophenyl, 2-methylphenyl, 3-methoxyphenyl, 3-methylphenyl or phenyl group.

2. The methods of claim 1 wherein said medicament further comprises at least on pharmaceutically acceptable carrier.

3. The method of claim 1 wherein said medicament further comprises additives selected from a group consisting of natural carbohydrates savoring agents, nutrients, vitamin, mineral (electrolyte), flavoring agents (synthetic and natural flavoring agent), colorant, filler (cheese, chocolate, etc), pectic acid and its salts, alginic acid and its salts, organic acid, protective colloidal thickener, pH modifier, stabilizer, antiseptic, antioxidant, glycerin, alcohol, carbonating agent, and pulp.

4. The methods of claim 1 wherein said medicament is formulated in a form selected from the group consisting of a powder, tablet, capsule, suspension, emulsion, syrup, aerosol, external application, suppository, and sterile injection.

5. The methods of claim 1 wherein said composition is administered to the patient at a dose ranging from between about 0.1 mg per kilogram of patient's body weight to about 500 mg per kilogram of patient's body weight.

6. The method of claim 1 wherein said medicament is formulated as various foods, gum, tea, vitamin complex supplements, and health care foods together with a sitologically acceptable additives.

7. The method of claim 6 wherein said composition is present in the food item in an amount ranging from about 0.1% to about 15% by weight of the food.

8. The method of claim 7 wherein said composition is present in the food item in a amount raging from about 1% to about 10% by weight of the food.

9. The method of claim 1 wherein said medicament is formulated as a beverage.

10. The method of claim 9 wherein said composition is present in the beverage is an amount ranging from about 1 g to about 30 g per 100 ml of beverage.

11. The method of claim 10 wherein said composition is present in the beverage in an amount ranging from about 3 g to about 10 g per 100 ml of beverage.

* * * * *